United States Patent [19]

George et al.

[11] Patent Number: 4,675,323

[45] Date of Patent: Jun. 23, 1987

[54] IMIDAZO(1,2-A)QUINOLINE DERIVATIVES USEFUL AS ANXIOLYTIC AGENTS

[75] Inventors: Pascal George, Vitry sur Seine, Belgium; Danielle De Peretti, Antony, France

[73] Assignee: Synthelabo, Paris, France

[21] Appl. No.: 826,981

[22] Filed: Feb. 7, 1986

Related U.S. Application Data

[63] Continuation-in-part of Ser. No. 763,009, Aug. 6, 1985, abandoned.

[51] Int. Cl.[4] ............... A61K 31/395; C07D 471/04; C07D 411/14; C07D 401/14
[52] U.S. Cl. .................................... 514/292; 546/84; 546/70; 514/285; 544/125; 544/126; 544/361
[58] Field of Search ............... 546/84, 70; 544/361, 544/126, 125; 514/292, 285

[56] References Cited

U.S. PATENT DOCUMENTS 4,387,098  6/1983  Barnes et al. ..................... 546/84

OTHER PUBLICATIONS

Goodman et al., The Pharmacological Basis of Therapeutics, 6 Ed., p. 28.

Primary Examiner—John M. Ford
Assistant Examiner—J. Richter
Attorney, Agent, or Firm—Wegner & Bretschneider

[57] ABSTRACT

Compounds which are imidazo[1,2-a]quinoline derivatives of general formula (I)

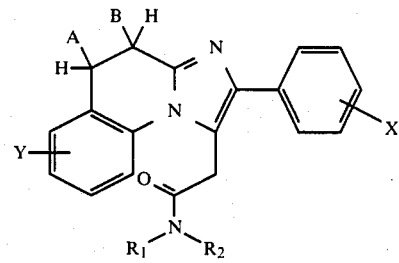

in which X is hydrogen, halogen, $(C_{1-4})$alkyl, $(C_{1-4})$alkoxy, $(C_{1-4})$ alkylthio, methylsulphonyl, amino, $(C_{1-4})$alkylamino, di-$(C_{1-4})$alkylamino, nitro or trifluoromethyl, Y is hydrogen, halogen or methyl in position 6, 7 or 8, $R_1$ and $R_2$, which may be the same or different, are hydrogen or $(C_{1-6})$ alkyl, or $R_1$ and $R_2$ together form a tetramethylene, pentamethylene, 3-methyl-3-azapentamethylene, 3-ethoxycarbonyl-3-azapentamethylene group, and A and B both are hydrogen or together form a carbon-carbon bond, and their pharmacologically acceptable acid addition salts have anxiolytic, sleep-inducing, hypnotic, anticonvulsant, analgesic and anti-ulcer properties.

6 Claims, No Drawings

IMIDAZO(1,2-A)QUINOLINE DERIVATIVES USEFUL AS ANXIOLYTIC AGENTS

This application is a continuation-in-part of U.S. Ser. No. 763,009 filed Aug. 6, 1985, now abandoned.

The present invention relates to imidazo[1,2-a]quinoline derivatives. According to the invention there are provided compounds which are imidazo[1,2-a]quinolines of the general formula

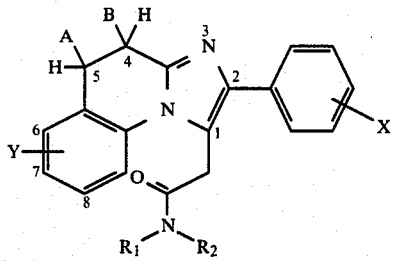

in which X is hydrogen, halogen, $(C_{1-4})$alkyl, $(C_{1-4})$alkoxy, $(C_{1-4})$alkylthio, methylsulphonyl, amino, $(C_{1-4})$alkylamino, di-$(C_{1-4})$alkylamino, nitro or trifluoromethyl, Y is hydrogen, halogen or methyl in position 6, 7 or 8, $R_1$ and $R_2$, which may be the same or different, are selected from hydrogen or $(C_{1-6})$alkyl, or $R_1$ and $R_2$ together form a tetramethylene, pentamethylene, 3-methyl-3-azapentamethylene, 3-ethoxycarbonyl-3-azapenta-methylene or 3-oxapentamethylene group, and A and B are both hydrogen or together form a carbon-carbon bond, and their pharmacologically acceptable acid addition salts.

The prefered compounds are those wherein X is chlorine, methyl or methylthio in position 4, Y is hydrogen, and $R_1$ and $R_2$ are independently to each other hydrogen or methyl. The compounds (I) can be prepared according to Scheme 1 illustrated on the following page. A quinoline of formula (II) is first subjected to the action of an α-bromo-acetophenone carrying the substituent X defined above. The reaction is suitably carried out in a solvent such as methylene chloride or 1,2-dichloroethane. An ionic compound of formula (III) is thus obtained, which is cyclized by heating in the presence of ammonium acetate and ferric chloride to produce a compound of formula (V) wherein A and B together form a carbon-carbon bond, or in the presence of ammonium acetate only to produce a compound of formula (V) wherein both A and B are hydrogen. A compound of formula (V) wherein AB is a bond can be obtained directly starting from a 2-aminoquinoline of formula (IV), subjected to the action of an α-bromoacetophenone carrying the substituent X, suitably in the presence of a base and in an alcoholic solvent. Formylation of compound (V) can be carried out e.g. by means of the reagent produced by reaction of oxalyl chloride with dimethylformamide, followed by hydrolysis of the suspected imminium adduct, and leads to the aldehyde (VI). The aldehyde (VI) thus obtained is then reduced to an alcohol of formula (VII), in a known manner, for example by reaction with sodium or potassium borohydride. The alcohol (VII) is then converted to the nitrile of formula (VIII). This can be done by subjecting the alcohol (VII) firstly to a tosylation, for example by means of para-toluenesulphonyl chloride, in the presence of pyridine, and then to the action of sodium or potassium cyanide in an aqueous medium. The nitrile (VIII) in then hydrolysed to a carboxylic acid in a known manner, for example by heating in a hydrochloric acid medium, to produce the acid of formula (IX). From this acid (IX), the corresponding amide of formula (I) is finally prepared. This can be done by subjecting the acid (IX) firstly to the action of carbonyldiimidazole, leading to the imidazolide, and then to the action of an amine of formula $R_1$—NH—$R_2$ in which $R_1$ and $R_2$ are as defined above.

Scheme 1

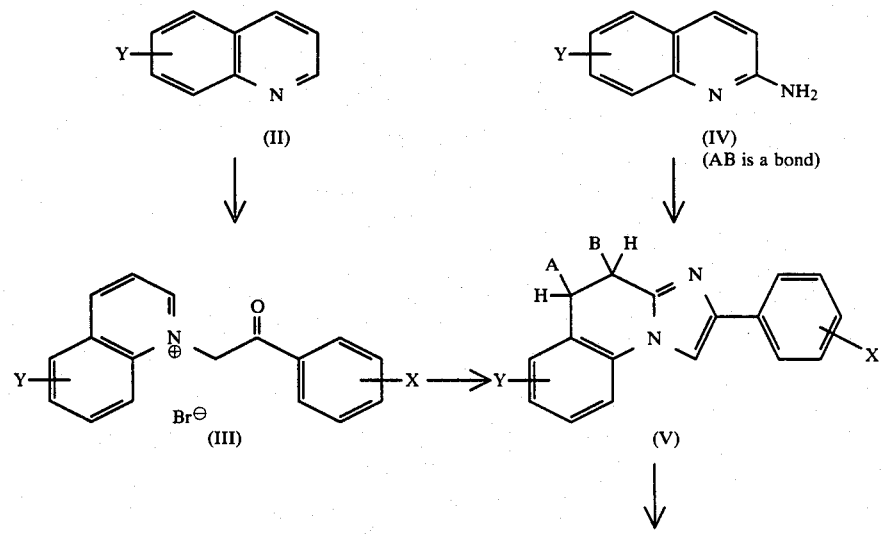

Scheme 1 -continued

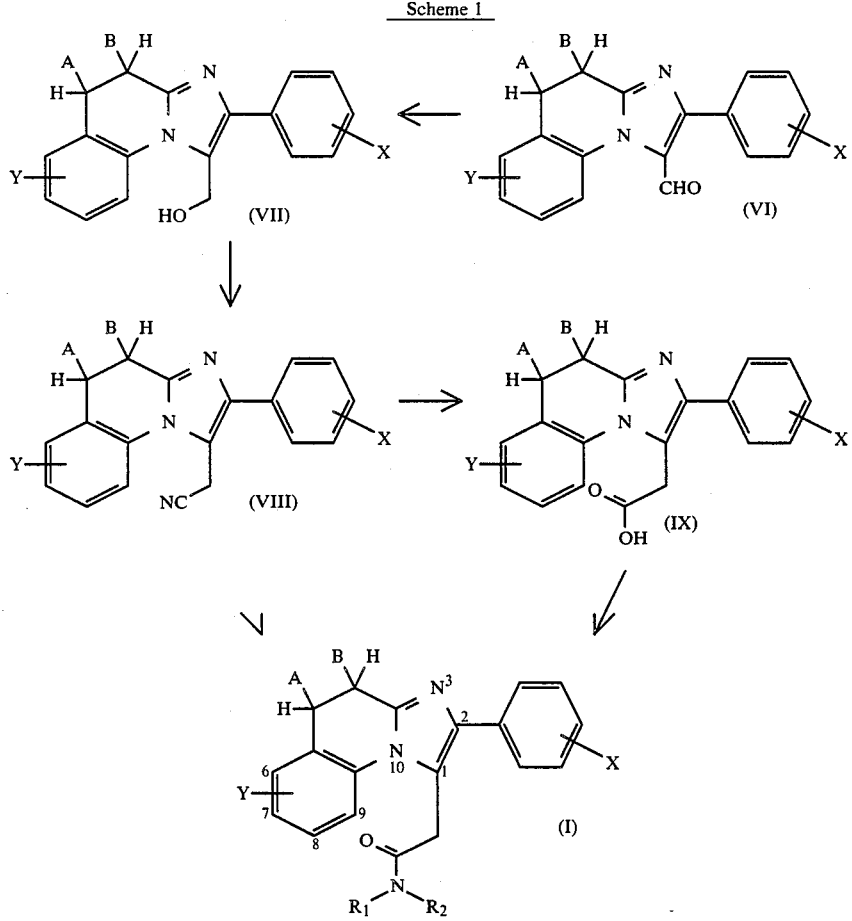

In the case of the unsubstituted amide of formula (I) in which both $R_1$ and $R_2$ are hydrogen, the final compound may be produced directly by partial hydrolysis of the nitrile (VIII) in an aqueous basic medium.

Another method according to the invention is shown in scheme 2 below. Accordingly the compound (V) is reacted with glyoxylic acid in a solvent such as acetic acid at a temperature of 80° C. The α-hydroxy-acid (X) thus obtained is acetylated by means of acetic anhydride in the presence of pyridine, then transformed into the α-acetoxy-acetamide (XI) via the imidazolide prepared in situ. Compound (XI) is then de-acetylated to produce the α-hydroxy-acetamide (XII) by reaction with potassium carbonate in a solvent such as ethanol. Compound (XII) is then reacted with sulfonylchloride in a chlorinated solvent such as methylene chloride to produce the chlorinated compound (XIII) which is finally reduced by means of Rongalite ® in methylene chloride to produce compound (I).

Lastly, it should be noted that the N,N-dimethylated amides of formula (I) can also be produced by methylation of the unsubstituted amide ($R_1=R_2=H$) by means of iodomethane in the presence of sodium hydride in the appropriate solvent.

Scheme 2

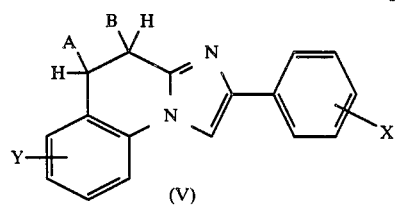

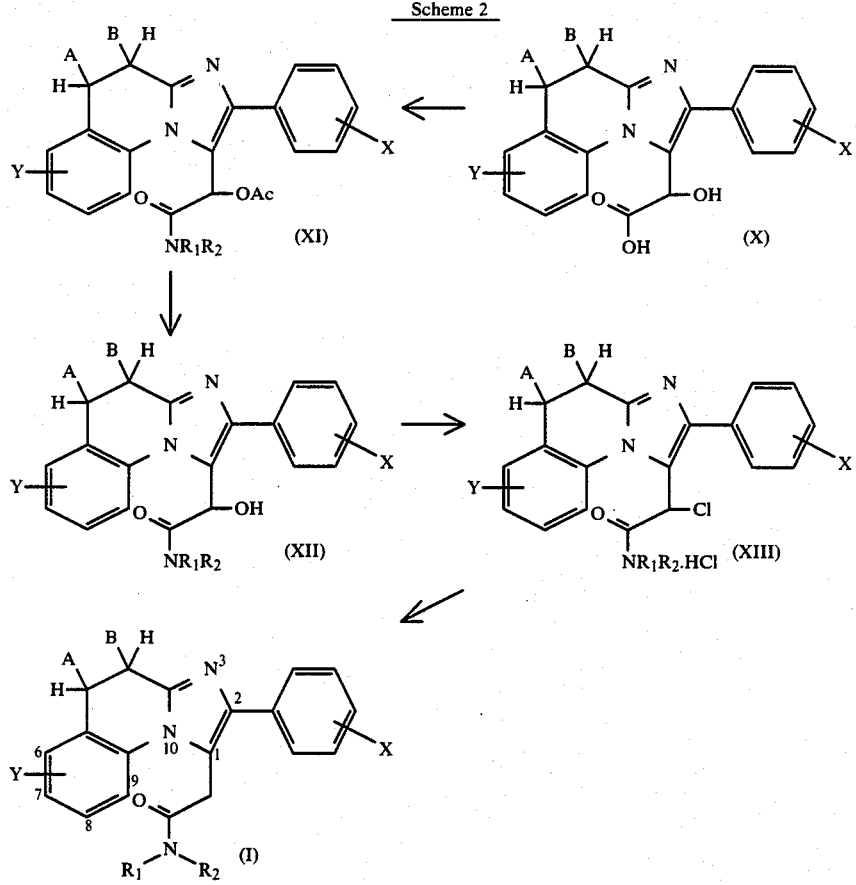

Scheme 2

Examples A and B below illustrate the two alternative ways of preparing the compound of formula (V).

The following examples illustrate the preparation of some compounds according to the invention. The structures of the compounds were confirmed by microanalyses and IR and NMR spectra.

EXAMPLE A 2-(4-Chlorophenyl)-imidazo[1,2-a]quinoline 17.7 g (0.123 mole) of 2-aminoquinoline, 28.7 g (1 equivalent of α-bromo-p-chloroacetophenone and 20.6 g (2 equivalents) of sodium bicarbonate are mixed in 180 ml of n-propanol and heated under reflux for 20 hours. The precipitate obtained is filtered off, washed with ethanol and water and dried. A white solid is obtained which is recrystallized from nitromethane.

M.p.: 206°–208° C.

EXAMPLE B 2-(4-Chlorophenyl)-imidazo[1,2-a]quinoline 23.3 g (0.1 mole) of α-bromo-p-chloroacetophenone and 13 ml (1.1 equivalent) of quinoline are mixed with 100 ml of methylene chloride. They are heated under reflux for 1 hour and then 100 ml of ether are added to the reaction mixture, which is cooled. The yellow precipitate obtained is filtered off and dried.

38.3 g (0.105 mole) of the above quaternary ammonium, 48.6 g (0.63 mole) of ammonium acetate, and 55 g (0.34 mole) of ferric chloride are mixed with 270 ml of acetic acid in a 1 liter autoclave, and are heated at 140° C. for 13 hours. The solid obtained is filtered off, washed with acetic acid and then with water; it is dried, and recrystallized from ethanol and then from nitromethane.

EXAMPLE 1

2-(4-Chlorophenyl)-1-imidazo[1,2-a]quinolylacetamide.

a. 2-(4-Chlorophenyl)-1 -imidazo[1,2-a]quinolylcarboxaldehyde 150 ml of dry dimethylformamide are cooled to −20° C. and 17.4 ml (0.2 mole) of oxalyl chloride are added dropwise. 13.6 g (0.05 mole) of the compound obtained according to Example A or B are then added and the mixture is stirred for 15 hours at ambient temperature and 15 hours at 55° C.

The mixture is then poured into 1 liter of water, the precipitate is filtered off and made alkaline, and washed with water to a neutral pH and dried. It is recrystallized from nitromethane.

M.p.=199°–200° C.

b.

1-Hydroxymethyl-2-(4-chlorophenyl)imidazo[1,2-a]quinoline.

13.3 g (0.043 mole) of the above aldehyde are suspended in 300 ml of dry absolute ethanol.

To this are added 825 mg (0.5 equivalent) of sodium borohydride and the mixture is stirred for 18 hours at ambient temperature. It is then evaporated to dryness, the residue is taken up with water, the pH is adjusted to 8 with dilute hydrochloric acid, and the precipitate is filtered off, washed with water, acetone and then with ether and dried.

M.p.=236°-237° C. (decomposition).

c. 1-Cyanomethyl-2-(4-chlorophenyl)imidazo[1,2-a]quinoline 7.8 g (0.025 mole) of the above alcohol and 5.3 g (1.1 equivalent) of p-toluenesulphonyl chloride are mixed in 100 ml of pyridine. The reaction mixture is heated at 40° C. for 8 hours and then stirred at ambient temperature for 60 hours. It is then taken up with 700 ml of water and 300 ml of methylene chloride, the precipitate between the two phases is filtered off and is dropped into 400 ml of water containing 3.7 g (0.075 mole) of sodium cyanide and 2.1 g (0.025 mole) of sodium bicarbonate. The mixture is heated under reflux for 15 hours and is then cooled and filtered. The precipitate is washed with water and extracted with methylene chloride and the extract is dried over sodium sulphate. The nitrile is purified by chromatography on silica gel.

After crystallization from ether and drying, a white solid is obtained.

M.p.=221°-223° C.

d. 2-(4-Chlorophenyl)-1-imidazo[1,2-a]quinolylacetamide 7 g (0.022 mole) of the above nitrile and 6 g (5 equivalents) of potassium hydroxide are mixed in 200 ml of ethanol and 50 ml of water, and heated for 3 hours under reflux. The mixture is then evaporated to dryness, the residue is taken up with water, filtered, washed with water to a neutral pH and dried.

M.p.=298°-300° C.

EXAMPLE 2

2-(4-Chlorophenyl)-1-imidazo[1,2-a]quinolyl-N-methylacetamide a. 2-(4-Chlorophenyl)-1-imidazo[1.2-a]quinolylacetic acid 3.5 g (0.011 mole) of the nitrile obtained according to Example 1c are dropped into a mixture of 10 ml of concentrated hydrochloric acid and 20 ml of acetic acid. This reaction mixture is heated under reflux for 8 hours, and then a further 10 ml of concentrated hydrochloric acid are added and heating under reflux is continued for 8 hours. The mixture is then evaporated to dryness, the residue is taken up with water, and the precipitate is filtered off. The precipitate is resuspended in water, the pH is adjusted to 5 with dilute sodium hydroxide, it is filtered, washed with ethanol, acetone and ether and is dried.

M.p.=246°-248° C. (decomposition).

b. 2-(4-Chlorophenyl)-1-imidazo[1,2-a]quinolyl-N-methylacetamide 2.5 g (0.0074 mole) of the above acid are suspended in 50 ml of dry tetrahydrofuran, 1.4 g (1.2 equivalent) of carbonyldiimidazole are added, and the mixture is heated at about 40° C. for 2 hours.

Methylamine is then bubbled through the mixture for 30 minutes and stirring is continued for 15 hours.

The mixture is evaporated to dryness, the residue is taken up with water and with methylene chloride, the organic phase is separated off, washed with water, dried and evaporated down. The residue is purified by chromatography and left to crystallize from ether.

M.p.=289°-292° C. (decomposition).

EXAMPLE 3

2-(4-Chlorophenyl)-1-imidazo[1,2-a]quinolyl-N,N-dimethylacetamide

To a suspension of 3.35 g (0.01 mole) of the compound obtained according to Example 1d in 200 ml of tetrahydrofuran are added 1.05 g (0.022 mole) of sodium hydride at a concentration of 50% in oil, 0.1 ml of dimethylformamide and then, rapidly, 1.9 ml (3 equivalents) of iodomethane. The mixture is stirred for 15 hours under argon at ambient temperature, and is then evaporated to dryness, the residue is taken up with water and with methylene chloride, the organic phase is washed with water, dried and evaporated down. The residue is purified by chromatography.

M.p.=190°-191.5° C.

EXAMPLE 4

2-(4-Chlorophenyl)-1-imidazo[1,2-a]quinolyl-N,N-tetramethyleneacetamide 2.5 g (0.0074 mole) of the acid obtained according to Example 2a are suspended in 50 ml of dry tetrahydrofuran, 1.4 g (1.2 equivalents) of carbonyldiimidazole are added, and the mixture is heated at about 40° C. for 2 hours. 0.63 g (1.2 equivalent) of pyrrolidine are then added and stirring is continued at ambient temperature for 15 hours. The mixture is evaporated to dryness, the residue is taken up with water and methylene chloride, the organic phase is separated off, washed with water, dried and evaporated down. The residue is purified by chromatography and left to crystallize from ether.

M.p.=217°-218° C.

EXAMPLE 5

N-methyl-2-(4-methylphenyl)-4,5-dihydro-imidazo[1,2-a]quinoline-1-acetamide (5.1) 110 g (0.516 mole) of α-bromo para-methyl acetophenone and 61 ml (0.516 mole) of quinoline are dissolved in 500 ml of methylene chloride. The solution is heated at reflux temperature for 1 hour and is then diluted with 300 ml of ether an cooled. After filtration and drying of the precipitate, a yellow solid is obtained. (M.p.=220°-221° C.

(5.2) 17.1 g (0.05 mole) of the quaternary salt obtained in (5.1) and 25 g of ammonium acetate are mixed in 50 ml of acetic acid. The suspension is heated for 3 hours at 90° C., is cooled, and is diluted with 200 ml of water. The brown precipitate formed is filtered and is taken up between water and methylene chloride. The biphasic mixture is treated with an excess of 1 N NaOH until pH<8. The organic phase is decanted, dried over $Na_2SO_4$, is filtered and the filtrate is concentrated under reduced pressure. The residue is recrystallized from pentane. 2-(4-methylphenyl)-4,5-dihydro-imidazo[1,2-a]quinoline (V) is thus obtained.

M.p.=91°-92° C. (decomposition).

(5.3) A mixture of 29 g (0.112 mole) of the 4,5-dihydroimidazo[1,2-a]quinoline, obtained in 5.2., 16.3 g (0.225 mole) of glyoxylic acid and 550 ml of acetic acid are heated for 6 hours at 80° C. The solution is concentrated under reduced pressure and the evaporation residue is taken up with water. The acid crystallizes, it is filtered, and then washed with water, then THF, then ether. It is dried under vacuum. The α-hydroxy acid (X) is obtained.

M.p. = 178°–181° C.

(5.4.1) 16.5 g (0.049 mole) of the α-hydroxy-acid are dissolved in 300 ml of a 50/50 mixture pyridine and acetic anhydride. The mixture is stirred overnight at room temperature and is concentrated under reduced pressure. The evaporation residue crystallizes by treatment with ether. The product obtained is used directly for the following step.

(5.4.2) 16.5 g (0.045 mole) of the α-acetoxy-acid obtained are reacted with 9.5 g (0.058 mole) of carbonyldiimidazole in 200 ml of dry THF. When no more gas is released, the solution is heated at 50° C. for 1 hour, is cooled, and is treated with an excess of dry gaseous methylamine. The reaction mixture is concentrated under reduced pressure, the residue is taken up between water and methylene chloride and is treated with $K_2CO_3$. The mixture is stirred 3 hours at ambient temperature and is decanted. The organic phase is dried over $Na_2SO_4$, is filtered and the filtrate is evaporated under reduced pressure. The resulting mixture is purified by silica chromatography and is crystallized in ether. The α-acetyloxyacetamide (XI) is obtained, which is deacetylated directly with no further purification.

(5.4.3) The α-acetyloxy-acetamide (XI) is treated with 25 g of $K_2CO_3$ in 100 ml of 50% aqueous methanol with stirring overnight. The solution is concentrated, the solid residue is taken up with water, is filtered and is washed with water until the pH of the wash water is neutral. It is then washed with ether and dried. The α-hydroxy-acetamide (XII) is thus obtained.

M.p. = 209°–211° C.

(5.5) 4.0 g (0.0115 mole) of the α-hydroxy-acetamide (XII) are treated with 25 ml of $SOCl_2$ in 125 ml of methylene chloride at room temperature overnight and the volatile residues are evaporated. The hydrochloride of the α-chloro-acetamide (XIII) is obtained. 100 g (0.0115 mole) of this compound are dissolved in 150 ml of $CH_2Cl_2$. The solution is treated with 5.3 g (0.0345 mole) of Rongalite ® at room temperature for 24 hours. At the end of the reaction, the mixture is filtered, the filtrate is concentrated under reduced pressure and the residue is treated with aqueous $NaHCO_3$. After several washes with water, the solid residue is filtered and dried. The crude mixture is purified by chromatography and is recrystallized from acetonitrile. The amide (I) is thus obtained.

M.p. = 226°–228° C.

EXAMPLE 6

N,N-dimethyl-2-(4-methylphenyl)-4,5-dihydro-imidazo[1,2-a]quinoline-1-acetamide (6.1.1) 16.5 g (0.049 mole) of the α-acetoxy acid obtained in (5.4.1) are reacted with 9.5 g (0.0585 mole) of carbonyl diimidazole in 200 ml of dry THF. When no more gas is released, the solution is heated at 50° C. for 1 hour, is cooled and is treated with an excess of dry gaseous dimethylamine. The mixture is stirred for several hours and is concentrated under reduced pressure. The evaporation residue is treated with aqueous $NaHCO_3$ and the α-acetoxy amide is extracted with $CH_2Cl_2$. It is purified by silica chromatography. An oil is obtained.

(6.1.2) The oil obtained in (6.1.1) above is treated wiht 45 g of $K_2CO_3$ dissolved in 100 ml of $CH_3OH$ at room temperature for 40 hours. After evaporating the water and methanol, the residue is taken up between water and methylene chloride. The organic phase is separated, dried over $Na_2SO_4$ and is filtered. The filtrate is concentrated under reduced pressure. The residual oil is crystallized from ether. The α-hydroxy-amide (XII) is thus obtained.

M.p. = 169°–170° C.

(6.2) 4 g (0.0115 mole) of the α-hydroxy acetamide (XII) are treated with 25 ml of $SOCl_2$ in 125 ml of $CH_2Cl_2$ at room temperature overnight. After evaporating the solvent and excess $SOCl_2$, the crude hydrochloride of the α-chloroacetamide is obtained, which is dissolved in 150 ml of $CH_2Cl_2$. This solution is treated with 5.3 g (0.0345 mole) of Rongalite ® at room temperature for 24 hours. At the end of the reaction, the suspension is filtered, the filtrate is concentrated under reduced pressure and the evaporation residue is treated with aqueous $NaHCO_3$. The insoluble solid is extracted with $CH_2Cl_2$ and is purified by chromatography (silica). It is recrystallized from ethyl acetate. The acetamide (I) is obtained.

M.p. = 206°–207° C.

The following table illustrates the structures and the physical properties of the compounds of the invention.

TABLE

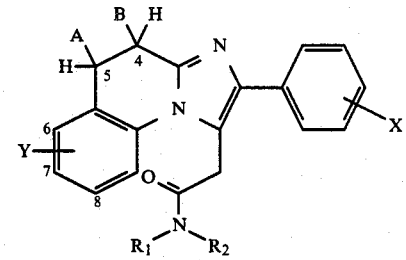

(I)

| Compound | A B (**) | Y | X | R1 | R2 | Base/salt(*) | M.p. (°C.) |
|---|---|---|---|---|---|---|---|
| 1 (Ex. 1) | — | H | 4-Cl | H | H | 00 | 298–300 |
| 2 (Ex. 2) | — | H | 4-Cl | H | $CH_3$ | 00 | 289–292 |
| 3 (Ex. 3) | — | H | 4-Cl | $CH_3$ | $CH_3$ | 00 | 190–191.5 |
| 4 (Ex. 4) | — | H | 4-Cl | —$(CH_2)_4$— | | 00 | 217–218 |
| 5 | — | H | 4-Cl | —$(CH_2)_5$— | | 00 | 163–164 |

TABLE-continued

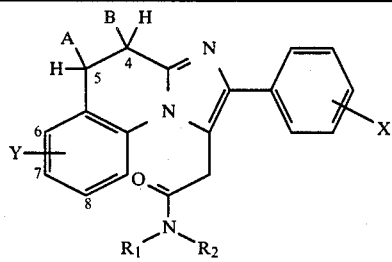
(I)

| Compound | A B (**) | Y | X | R1 | R2 | Base/salt(*) | M.p. (°C.) |
|---|---|---|---|---|---|---|---|
| 6 | — | H | 4-Cl | —(CH$_2$)$_2$—N—(CH$_2$)$_2$—<br>\|<br>CH$_3$ | | 15 | 162–165 |
| 7 | — | H | 4-Cl | —(CH$_2$)$_2$—N—(CH$_2$)$_2$—<br>\|<br>COOC$_2$H$_5$ | | 00 | 188–190 |
| 8 | — | H | 4-Cl | —(CH$_2$)$_2$—O—(CH$_2$)$_2$— | | 00 | 228–232 |
| 9 | — | H | 4-Cl | H | C$_2$H$_5$ | 00 | 268–270 |
| 10 | — | 8-Cl | 4-Cl | H | CH$_3$ | 00 | 290.5–291 |
| 11 | — | 8-Cl | 4-Cl | CH$_3$ | CH$_3$ | 00 | 259–260 |
| 12 | — | 7-Cl | 4-Cl | H | CH$_3$ | 00 | 300–302 |
| 13 | — | 7-Cl | 4-Cl | CH$_3$ | CH$_3$ | 00 | 248–250 |
| 14 | — | 6-Cl | 4-Cl | H | CH$_3$ | 00 | 306–307 |
| 15 | — | 6-Cl | 4-Cl | CH$_3$ | CH$_3$ | 00 | 248–249 |
| 16 | — | 7-F | 4-Cl | H | CH$_3$ | 00 | 304–305 |
| 17 | — | 7-CH$_3$ | 4-Cl | H | CH$_3$ | 00 | 269–271 |
| 18 | — | H | 4-CH$_3$ | H | CH$_3$ | 00 | 265–266 |
| 19 | — | H | 4-CH$_3$ | CH$_3$ | CH$_3$ | 00 | 181–182.5 |
| 20 | — | H | 4-OCH$_3$ | H | CH$_3$ | 00 | 264–265 |
| 21 | — | H | 4-OCH$_3$ | CH$_3$ | CH$_3$ | 00 | 194–196 |
| 22 | — | H | 4-SCH$_3$ | H | CH$_3$ | 00 | 284–287 |
| 23 | — | H | 4-SCH$_3$ | CH$_3$ | CH$_3$ | 00 | 172–173 |
| 24 | — | H | 3-Cl | H | CH$_3$ | 00 | 261–262 |
| 25 | — | H | 3-Cl | CH$_3$ | CH$_3$ | 00 | 138–140 |
| 26 | — | H | 2-Cl | H | CH$_3$ | 00 | 222–224 |
| 27 | — | H | 2-Cl | CH$_3$ | CH$_3$ | 00 | 165–167 |
| 28 | — | H | H | H | CH$_3$ | 00 | 264–266 |
| 29 | — | H | H | CH$_3$ | CH$_3$ | 00 | 173–175 |
| 30 | — | H | 4-SO$_2$CH$_3$ | H | CH$_3$ | 00 | 279–280 |
| 31 | — | H | 4-SO$_2$CH$_3$ | CH$_3$ | CH$_3$ | 00 | 244–245 |
| 32 (Ex. 5) | H H | H | 4-CH$_3$ | H | CH$_3$ | 00 | 226–228 |
| 33 (Ex. 6) | H H | H | 4-CH$_3$ | CH$_3$ | CH$_3$ | 00 | 206–207 |
| 34 | H H | H | 4-Cl | H | CH$_3$ | 00 | 236–237 |
| 35 | H H | H | 4-Cl | CH$_3$ | CH$_3$ | 00 | 193–194 |
| 36 | H H | H | 4-SCH$_3$ | H | CH$_3$ | 00 | 245–247 |

(*): 00 denotes the free base, 15 the methanesulphonate salt.
(**): — denotes a C—C bond.

The compounds of the invention have been the subject of pharmacological tests which have demonstrated their interest as substances with therapeutic activities.

Antagonism towards clonic convulsions induced by Cardiazol ® in the mouse.

The test is prompted by the protocol described by Goodman et al., J. Pharm. Exp. Ther., 108, 168–176. The mice receive the products to be tested, or the solvent alone, 30 minutes (i.p. route) or 60 minutes (oral route) before the injection of 35 mg/kg of Cardiazol ® by intravenous route. The animals are then observed for one hour and, for each batch, the percentage of mice presenting clonic convulsions is noted (100% of clonic convulsions and 10 to 20% of tonic convulsions in th control animals). The percentage of protection in comparison with the control animals is calculated for each dose, which makes it possible to determine graphically the AD$_{50}$, the dose which protects 50% of the animals against the convulsion-inducing action of Cardiazol ®. The AD$_{50}$s of the compounds of the invention are between 0.1 and 30 mg/kg for the intraperitoneal route and between 0.1 and 30 mg/kg for the oral route.

"Burying test" in the mouse.

This test is prompted by the method described by J. P. J. Pinel, D. Treit, F. Ladak and A. J. MacLennan in Animal Learning and behavior, 8, 447–451, (1980).

The presence of foreign bodies in the usual environment of an animal forms an aversive situation to which the animal reacts by burying the aggressive object (glass beads) in the sawdust in its cage.

The effect of anxiolytics is to reduce the fear caused by the foreign presence: the animals bury less. The number of unburied beads which remain is then counted.

The products to be studied are administered to male CD1 strain (Charles River) mice 30 minutes (intraperitoneal route) or 60 minutes (oral route) before the latter are placed in cages containing 25 glass beads. After 30 minutes the number of beads remaining unburied is counted. A percentage is calculated for the treated animals and the control animals.

In this way the AD50 is determined, the 50% active dose, which is the dose of the compound (in mg/kg) reducing by half the number of buried beads, in comparison with the control animals. The $AD_{50}s$ of the compounds of the invention are between 0.3 and 30 mg/kg by intraperitoneal route.

The drink conflict test in the rat.

This test is described by J. R. Vogel, B. Beer and D. E. Clody in Psychopharmacologia, 21, 1–7, (1971)

Male Wistar rats (IFFA Credo) are employed. Their drinking water is withdrawn 24 h before the test. On the day of the test, 30 minutes after treatment with the compounds of the invention by intraperitoneal route, each rat is placed in a transparent plastic cage (24×20×21 cm) with a gridded floor which can be electrified. Drinking water is distributed by means of a pipette projecting 2 cm from a cage wall and placed 3 cm above the cage floor.

After an exploration lasting 10 to 90 seconds, the animal finds the pipette and begins to drink. After having made 20 flicks of the tongue (which are recorded by an Omnitech anxiometer), the rat receives a 0.07 mA electric shock (delivered by the anxiometer) at the tongue, which ceases when the rat leaves the pipette. A 3-minute session begins after a first shock, the animal continuing to receive a shock every 20 flicks of the tongue until it stops or until the end of the session.

Under these experimental conditions, the control animals tolerate, on average, 3 to 6 shocks. The number of shocks obtained with the treated animals is noted, and this number is compared with that for the control animals using a Dunett test. This is used to determine the $MED_,$, the minimum effective dose, which is the first dose which increases significantly the number of shocks tolerated by an animal, relative to the controls. The MEDs are between 3 and 100 mg/kg by an intraperitoneal route. Effect on the electrocorticogram of the ventilated curarised rat.

The sedative or hypnotic activity of the compounds has been determined by observing their effect on the electrocorticogram of the rat according to the method described by H. Depoortere, Rev. E.E.G. Neurophysiol., 10, 3, 207–214 (1980) and by H. Depoortere and M. Decobert, J. Pharmacol. (Paris), 14, 2, 195–265 (1983).

The products to be studied were administered by the intraperitoneal route in doses increasing from 1 to 30 mg/kg.

They induce sleep traces starting with doses ranging from 3 to 100 mg/kg.

Effects on the duration of "sleep" induced by sodium 4-hydroxybutyrate.

This action was determined by the effect of a compound on the duration of "sleep" induced by sodium 4-hydroxybutyrate (GHB) in the curarized rat.

The animals employed are Charles River strain male rats 200±20 g in weight. The animals, curarized with Alloferin in a dose of 1 mg/kg by i.p. route, are placed under artificial respiration with the aid of a mask placed over the muzzle (frequency of respiration=50/minute; respiratory volume=14 ml).

The oesophagus is ligatured beforehand to prevent the entry of air into the stomach.

Frontoparietal and occipital cortical electrodes make it possible to record the electrocorticographic activity on a Grass multipoint recorder model 79 P at a speed of 6 mm/s.

The preparation of the animal is carried out under local anaesthesia (2% Xylocaine). The rats are kept at a constant temperature (37.5° C.) throughout the experiment. Ten minutes after the rat's preparation has been completed a 200 mg/kg dose of sodium 4-hydroxybutyrate is injected by intravenous route at the tail.

A 10 mg/kg dose of the compound under study is administered by intraperitoneal route 3 minutes after the administration of sodium 4-hydroxybutyrate.

The evaluation of the traces is carried out over 15-minute periods for 75 minutes after the injection of GHB. During this analysis period, the total duration of "sleep" is determined. A series of 15 controls makes it possible to establish precisely the duration of "GHB sleep".

Statistical analysis of the results is carried out using the Mann-Whitney "U" test.

Some compounds reduce the effects of GHB (up to 24% reduction in the duration of sleep at a dose of 10 mg/kg), while others intensify these effects (up to 18% increase in the duration of sleep at a dose of 10 mg/kg, or 30% at a dose of 30 mg/kg). It is also found that the effects can be oposite, depending on whether the compounds are administered in high doses or low doses.

Stress-induced ulcer

The technique used is that of Senay and Levine, Pro. Soc. Exp. Biol. 1967, 124, 1221–1223 and Peptic Ulcers, edited by C. J. PFEIFER, pp. 92–97, on Wistar female rats weighing 120–210 g, fasted for 20 hours and distributed in random groups.

The animals are put under restraint in cylindrical boxes 20 cm×5 cm, and placed in a cold room in which the temperature is maintained at 2°–4° C.

The compounds to be studied are administered orally in the proportion 10, 30 and 100 mg/kg immediately before putting the animals under restraint, the control rats receiving only the placebo.

2 hours later, the animals are sacrificed by inhalation of chloroform.

The stomachs are removed and the degree of ulceration noted. The compound of the invention significantly reduced the stress-induced ulcers.

Analgesic activity

The analgesic activity of the compounds was shown by the "writhing" test described by Koster et al (Fed. Proc., 18, 412, 1959). Fasting mice were administered to with the compounds dissolved at 1% in Tween 80, at a dose of 0.2 ml per 20 g of body weight; 30 minutes later acetic acid (a 0.6% solution in a mixture of carboxymethyl-cellulose and Tween 80, at a dose of 10 ml/kg of body weight) is injected intraperitoneally. The number of writhings is counted within 15 minutes.

The percentage of protection is determinated with respect to control animals, and the "effective dose 50 percent" ($ED_{50}$) is calculated graphically.

The $ED_{50}$ of the compounds of the invention is in the range of 0.1 to 30 mg/kg. The results of these various tests show that the compounds of the invention have anxiolytic, sleep-inducing, hypnotic, anticonvulsant, analgesic and anti-ulcer properties; the compounds of the invention are useful for the treatment of anxiety states, disturbances of sleep and other neurological and psychiatric disorders, for the treatment of disturbances of vigilance, in particular for combating behaviour disturbances attributable to cerebral vascular damage and to cerebral sclerosis in geriatrics, and for the treatment of absences due to cranial traumas, for the treatment of metabolic encephalopathies, and for the treatment of ulcer and various pains and aches.

The compounds of the invention may be presented in any form suitable for administration by oral or parenteral route, for example in the form of tablets, pills, gelatine capsules, drinkable or injectable solutions, and the like, in combination with any suitable excipient.

The daily dosage can range from 1 to 100 mg.

We claim:

1. Imidazo[1,2-a]quinolines of the general formula (I)

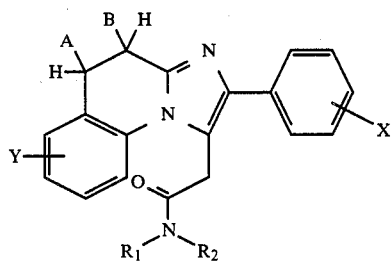

in which

X is selected from hydrogen, halogen, $(C_{1-4})$alkyl, $(C_{1-4})$alkoxy, $(C_{1-4})$alkylthio, methylsulphonyl, amino, $(C_{1-4})$alkylamino, di-$(C_{1-4})$alkylamino, nitro or trifluoromethyl, Y is selected from hydrogen, halogen or methyl in position 6, 7 or 8, $R_1$ and $R_2$, which may be the same or different, are selected from hydrogen, or $(C_{1-6})$alkyl, or $R_1$ and $R_2$ together form a group selected from tetramethylene, pentamethylene, 3-methyl-3-azapentamethylene, 3-ethoxycarbonyl-3-azapentamethylene and 3-oxapentamethylene, and A and B are both selected from hydrogen or together form a carbon-carbon bond, and their pharmacologically acceptable acid addition salts.

2. A compound according to claim 1, in the formula (I) of which X is chlorine, methyl or methylthio, Y is hydrogen, and $R_1$ and $R_2$ each are hydrogen or methyl.

3. An anxiolytic pharmaceutical composition which comprises an anxiolytically effective amount of a compound as claimed in claim 1 in association with a pharmaceutically acceptable excipient.

4. A sleep-inducing or hypnotic pharmaceutical composition which comprises a sleep-inducing or hypnotic effective amount of a compound as claimed in claim 1 in association with a pharmaceutically acceptable excipient.

5. An anti-ulcer pharmaceutical composition which comprises an anti-ulceratively effective amount of a compound as claimed in claim 1 in association with a pharmaceutically acceptable excipient.

6. An anticonvulsant pharmaceutical composition which comprises an anticonvulsant effective amount of a compound as claimed in claim 1 in association with a pharmaceutically acceptable excipient.

* * * * *